United States Patent [19]

Martini

[11] 4,035,388

[45] July 12, 1977

[54] PROCESS FOR PREPARING PERFLUORO-ALKOXY-PROPIONIC ACID FLUORIDES

[75] Inventor: Thomas Martini, Neuenhain, Taunus, Germany

[73] Assignee: Hoechst Aktiengesellschaft, Frankfurt am Main, Germany

[21] Appl. No.: 643,124

[22] Filed: Dec. 22, 1975

[30] Foreign Application Priority Data

Dec. 24, 1974 Germany .......................... 2461445

[51] Int. Cl.$^2$ ................. C07D 319/12; C07C 51/58
[52] U.S. Cl. ......................... 260/340.6; 260/544 F
[58] Field of Search ......... 260/535 H, 340.6, 544 F

[56] References Cited

U.S. PATENT DOCUMENTS

| 3,140,296 | 7/1964 | McClure | 260/340.6 |
| 3,250,808 | 5/1966 | Moore et al. | 260/535 H |
| 3,274,239 | 9/1966 | Selman | 260/535 H X |
| 3,321,517 | 5/1967 | Selman | 260/535 H X |

FOREIGN PATENT DOCUMENTS

| 707,361 | 4/1965 | Canada | 260/535 H |
| 1,038,193 | 8/1966 | United Kingdom | 260/535 H |

*Primary Examiner*—Ethel G. Love
*Attorney, Agent, or Firm*—Curtis, Morris & Safford

[57] ABSTRACT

Perfluoro carbonyl compounds react with hexafluoro propene epoxide in the presence of dimethylamino-difluoro-phosphorane producing perfluorinated carboxylic acid fluorides with ether linkages. Among the carbonyl compounds which can be used are perfluorinated ketones, acid fluorides of the formula $R_F$ — COF and $R_F$ — OCF(CF$_3$) — COF ($R_F$ being a perfluoro-alkyl radical having from 1 to 4 carbon atoms) and perfluoro-2-oxo-3,6-dimethyl-1,4-dioxane.

9 Claims, No Drawings

PROCESS FOR PREPARING PERFLUORO-ALKOXY-PROPIONIC ACID FLUORIDES

The present invention relates to the preparation of perfluoro- α-alkoxypropionic acid fluorides by means of hexafluoropropene epoxide (HFPO). Perfluoro-α-alkoxypropionic acid fluorides may be employed as intermediate products for preparing perfluorinated vinyl ethers, e.g. according to the process of British Pat. No. 1,145,445. The copolymerization of these vinyl ethers, e.g. according to the process of U.S. Pat. No. 3,484,503 is very important. Moreover, perfluoro-α-alkoxypropionic acid fluorides are interesting starting materials for the polymerization of tetrafluoroethylene epoxide or hexfluoropropene epoxide (e.g. according to German Pat. No. 1,234,702).

Several processes are known for the preparation of α-alkoxy-propionic acid fluorides:

German Offenlegungsschrift 2,026,669 describes the dimerization of HFPO in the presence of silver nitrate. This process yields almost exclusively perfluoro-α-propoxypropionic acid fluoride. Only minor quantities of high-molecular weight oligomers of HFPO are formed simultaneously.

According to U.S. Pat. 3,114,778 one mole of HFPO per COF group may be added to perfluoarocarboxylic acid fluorides, in the presence of catalysts, whereby alkoxycarboxylic acid fluorides are formed. The yields are sometimes poor. The process according to U.S. Pat. No. 3,274,239 provides for adding HFPO to per-fluoroketones at a temperature of from +50° C to +80° C in a pressure vessel and in the presence of an alkali fluoride catalyst, but this method yields — depending on the reaction conditions — either monoaddition products only or large portions of material with high molecular weight. Therefore, this process does not enable the isolation of noticeable portions of addition products having 2 or 3 moles of HFPO.

These addition products of HFPO of higher molecular weight may be converted to vinyl ethers and then employed for building up copolymers.

Therefore, the aim had to be to find a process which allows for one thing to produce a portion as high as possible of diaddition products having formula $R_FOCF(CF_3) CF_2 — O — CF (CF_3) — COF$ or of triaddition products having formula

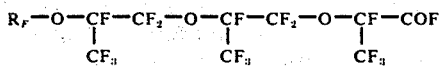

and, on the other hand, to keep low the portion of oligomers with even higher molecular weight.

A further aim was a process for the addition of HFPO to perfluoro-carboxylic acid fluorides, which would be independent of the expensive catalysts silver nitrate and caesium fluoride and especially which could be carried out without applying high pressure.

Subject of the present invention is a process for preparing perfluoro-α-alkoxypropionic acid fluorides of general formula

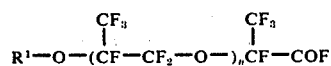

wherein $R^1$ stands for a perfluoroalkyl radical having from 1 to 9 carbon atoms or for the radical

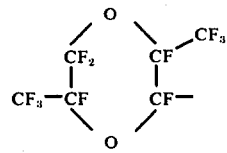

and wherein $n$ means 0, 1 or 2, which comprise that perfluorocarbonyl compounds of general formula

in which $R^2$ means fluorine or $R_F^2$,
$R^3$ means fluorine or $R_F^3$ or (if $R^2$ is fluorine), also $R_F^2 — OC_F (CF_3)—$,
$R_F^2$ and $R_F^3$ mean equal or different perfluoroalkyl radicals having from 1 to 4 carbon atoms, or wherein
$R^2$ and $R^3$ together with the group CO yield the compound perfluoro- 2-oxo-3,6-dimethyl-1,4-dioxane, react with hexafluoropropene epoxide in the presence of tris-dimethylamino-difluoro-phosphorane in an aprotic polar solvent at temperatures of from −50 to −10° C.

If $R^2$ if fluorine, $R^3$ may be fluorine, $R_F^3$ or $F_F^3—OC(CF_3)—$. If $R^2 = R_F^2$, $R^3$ may be fluorine or $R_F^3$. Especially interesting starting compounds are those having formula $R^2 — CO— R^3$, wherein $R^2$ and $R^3$ are not fluorine at the same time. From these starting compounds may be prepared acid fluorides having formula I, wherein $R^1$ stands for a perfluoro alkyl radical having from 2 to 9 carbon atoms.

The operations take place preferably at temperatures of from − 40° to −20° C.

According to the process of the invention 1 − 3 moles of hexafluoropropene epoxide are added to a carbonyl compound, so that the formation of product mixtures is also possible. However, by reducing the ratio HFPO/carbonyl compounds, a tendency towards the monoaddition product may be favored. In a similar way, the addition of more than 1 mole of HFPO/mole of carbonyl compound is favored by raising this ratio and extending the reaction period.

The process according to the invention may be illustrated by the following selected equations:

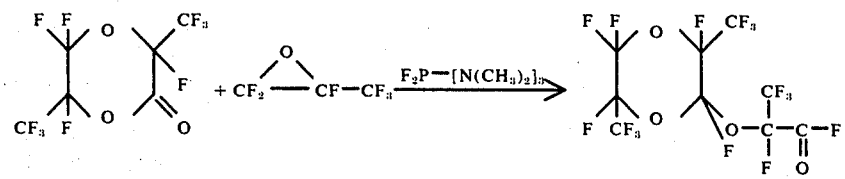

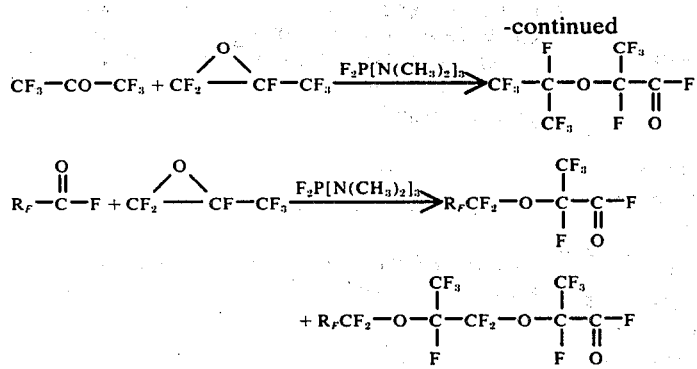

The process is generally carried out in such a way, that hexafluoropropene epoxide, optionally blended with hexafluoropropene (HFP) is introduced at reaction temperature into the solution of the compound having formula II in a aprotic solvent, in the presence of tris-dimethylamino-difluoro-phosphorane.

The rate, at which the epoxide is added, is not of critical importance. There is even the possibility to add the required quantity at once, provided that care is taken for a sufficient heat transfer. Generally, there are utilized per mole of carbonyl compound one or two moles of HFPO. An excess surpassing this rate is often advantageous, especially when compounds of formula I have to be prepared in which $n$ means 1 or 2; for such an excess encourages the reaction to attain a conversion rate as high as possible. Said excess may generally amount to 300% or more, preferably up to 150% - calculated on the stoichiometric quantity. After the reaction, the excess is completely recovered in practice.

The solvents or solvent mixtures which may be utilized for the process, have to be polar, aprotic and, under the reaction conditions, inert and liquid. Suitable are, for example, nitriles, dimethylformamide, preferably ethers such as ethylene glycol dimethyl ether, diethylene glycol dimethyl ether or tetraethylene glycol dimethyl ether. The quantity of the employed solvent is not of critical importance, provided that the reaction mixture can be mixed thoroughly at the temperature applied and provided that the viscosity does not rise too high. Possible ratios are 0.15 – 10, especially 0.25 – 4 parts by volume of solvent per part by weight of carbonyl compound, the part of volume in relation to the part by weight corresponding to ml : g.

The process may be carried out either batchwise or continuously. After a certain reaction time, the reaction product which is separating a heavier phase, may be eliminated and the introduction of the reactants continued further. The difluorophosphorane which is dissolved in the solvent remains in the reactor and acts as a genuine catalyst.

The quantity at which the catalyst is employed is not of critical importance. There may be utilized quantities of 0.05 to twice the molar quantity, calculated on the carbonyl compounds to be reacted. The preferred amounts keep rather within the lower range of said interval in case of using keto-compounds of formula II, preferably at 0.1 to 0.5 mole per mole; in case of using acid fluorides the range keeps rather within the upper interval, preferably at 0.6 to 1.5 mole, per mole of employed carbonyl compound. Larger quantities are possible, but do not represent any advantage.

After termination of the reaction the temperature is raised to $-5°$ to $-10°$ C in case that the operations were carried out with excess HFPO or with a hexafluoropropene-containing mixture.

The part of the HFPO which did not participate in the reaction, is discharged in its gaseous state (optionally together with hexafluoropropene) and can be recovered on that occasion. The reaction products may be distilled directly or, advantageously, washed prior to the distillation with a suitable aprotic polar solvent, such as acetonitrile. In case that the boiling point of the solvent and of the synthesized perfluoro compound differ clearly, this fact leads to particularly pure products.

Starting products for the process of the invention are perfluorinated acid fluorides or ketones. Suitable acid fluorides are for example perfluoroacetyl fluoride, perfluoropropionic acid fluoride or perfluorobutyryl fluoride, but also acid fluorides containing already an ether group, such as perfluoro-α-propoxy-propionic acid fluoride. As examples for suitable ketones may be cited: hexafluoroacetone or perfluoromethylbutyl ketone as well as perfluoro-2-oxo-3,6-dimethyl-1,4-dioxane. These starting compounds of formula II are accessible according to known processes. In some cases (e.g. perfluoro-α-propoxypropionic acid fluoride) they may be obtained even from ketone or acid fluoride with HFPO according to the process of the invention. In other cases, it may be sufficient to prepare in situ the starting products of formula II under the conditions of the process according to the invention and to have them react further with hexafluoropropene epoxide. In that way, hexafluoropropene epoxide - without addition of a carbonyl compound - probably forms perfluoro-α-n-propoxypropionic acid fluoride which immediately continues to react further with epoxide according to the process of the invention to yield perfluoro-α-[-2-(n-propoxy)-propoxy]-propionic acid fluoride. The same spectrum of final products is obtained, when perfluoro-n-propionic acid fluoride as starting product reacts with hexafluoro-propene epoxide. The result is in the both cases a mixture of compounds of general formula I.

The starting compound perfluoro-2-oxo-3,6-dimethyl-1,4-dioxane may be prepared analogously in situ from perfluoropyruvic acid fluoride and HFPO and converted immediately with further HFPO to yield the corresponding propionic acid derivative.

This embodiment of the process according to the invention is especially interesting, when a molar ratio of HFPO/perfluoropyruvic acid fluoride of from 1.0 to 5, preferably from 1.5 to 3, is applied. In this case the following reaction takes place:

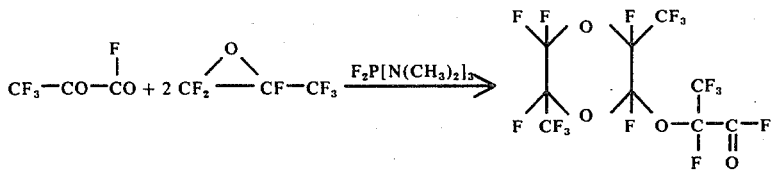

The inert ether of formula

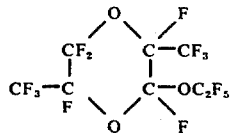

is obtained from this pripionic acid fluoride derivative by saponification and decarboxylizing fluorination in known manner.

This perfluoro-3,6-dimethyl-2-ethoxy-dioxane-1,4 has a boiling point of 98° to 101° C. The compound is appropriate, for example, as lubricant, sealing fluid, heat transfer substance, insulation fluid or hydraulic liquid.

The process according to the invention is especially suitable for preparing such compounds of formula I, wherein n is 0 or 1. Due to their higher reactivity especially suitable starting products are such compounds of formula II, wherein $R_2$ and $R_3$ are not fluorine, namely the ketocompounds. The reacting opacity of the obtained acid fluorides of formula I decreases with $n$ increasing. An addition of more than 3 moles of epoxide per mole of carbonyl compound can be observed only to a very limited extent under technically reasonable conditions.

In case of ketones are preferably employed as starting substances those compounds of formula II, in which $R_F{}^2$ or $R_F{}^3$ represent perfluoro-n-alkyl groups. Branched radicals such as perfluoro-isopropyl and especially perfluoro-tert.-butyl adjacent to the carbonyl function induce a low reaction speed so that e.g. compounds such as methyl-tert.-butyl-ketone according to the process of the invention react very slowly.

The following examples illustrate the invention:

EXAMPLE 1

250 g of perfluoro-2-oxo-3,6-dimethyl-1,4-dioxane (0.806 mole) are added at from −40° to −30° C - while agitating constantly - to a solution of 50 g of tris-dimethylaminodifluoro- phosphorane (0.249 mole) in 150 ml of diglyme which had been charged into a three-necked flash equipped with agitator, intensive coller and frigothermometer; agitation is then continued for another hour. At the above specified temperature 250 g of HFPO-HFP-mixture (weight ratio 65:35) are introduced and condensed (20 1/h). The intensive agitation is continued for 5 hours. HFP and excess epoxide are evacuated by heating slowly to 0° C and the thus obtained two-phase-mixture is separated in a separatory funnel. The lower phase is submitted to distillation after washing with 100 ml of acetonitrile.

293 g of perfluoro-α-(3,6-dimethyl-1,4-dioxanyl-2-oxy)- propionic acid fluoride are obtained having a boiling point of 115°-118° C (76.4% of the theoretical yield). A quantity of 30 g remains as a residue having a higher boiling point. No more starting material is present.

EXAMPLE 2

The procedure of example 1 was prepeated but the perfluorodioxane used in example 1 was prepared in situ. Into the apparatus of example 1 was charged a solution of 50 g of tris-dimethylaminodifluorophosphorane (0.249 mole) in 90 ml of diethylene glycol dimethyl ether (diglyme). At a temperature of from −40° to −+° C 63 g of perfluoropyruvic acid fluoride (0.437 mole) are introduced and condensed while agitating constantly. Agitation is continued for another hour at the same temperature and 220 g of a gaseous mixture of HFPO and hexafluoropropene (HFP) (weight ratio 65:35) metered in at the rate of 20 1/h. Agitation is further continued for 3 hours. By slowly heatng to 0° C HFP and excess epoxide are evacuated and the two-phase mixture separated in the separatory funnel. The lower phase is washed with 100 ml of acetonitrile and submitted to distillation. 127 g of perfluoro-α-(3,6-dimethyl-1,4-dioxanyl-2-oxy)-propionic acid fluoride (boiling point 115° − 118 C are obtained. The portion having a higher boiling point amounts to 24 g. The upper phase containing the catalyst may be recycled.

EXAMPLE 3

The apparatus as used in example 1 is charged with a solution of 40 g of tris-dimethylaminodifluorophosphorane (0.199 mole) in 150 ml of diglyme. A portion of 163 g of hexafluoroacetone (0.982 mole) is added by condensation while agitating constantly at temperatures of from −40° to −30° C. After having agitated intensely for one hour, while maintaining the same temperature, 335 g of a mixture of HFPO-HFP (weight ratio 65:35) are introduced and agitated for 4 hours. The lower phase being separated at 0° C is distilled directly. 240 g of perfluoro-α-isopropoxypropionic acid fluoride having a boiling point of from 56° − 57° C are obtained (73.7% of the theoretical yield). A quantity of 39 g remains as a residue having a higher boiling point.

EXAMPLE 4

In analogy to example (1) 200 g of perfluoro-α-propoxypropionic acid fluoride (0.602 mole) are added slowly at −40° to −30° C to a solution of 100 g of tris-dimethylaminodifluorophosphorane (0.498 mole) in 70 ml of diglyme, agitation is then continued for another hour. Subsequently, while maintaining the same temperature, 550 g of a mixture of HFPO/HFP (weight ratio 65:35) are metered in at the rate of 20 1h, agitation is continued for further 9 hours at the afore specified temperature. The work-up is carried out according to example (1); after distilling off the portions having a low boiling point there are obtained 108 g of perfluoro-α-[2-(n-propoxy)- propoxy]-propionic acid fluoride having a boiling point of 115° − 117° C (36% of the theoretical yield).

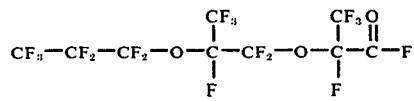

27 g of portions having a higher boiling point are obtained.

EXAMPLE 5

110 g of perfluoropropionic acid fluoride (0.663 mole, diluted with 90 g of hexafluoropropene, are introduced at the rate of 20 l/h into an apparatus as per example 1, charged with a solution of 150 g of tris-dimethylaminodifluorophosphorane (0.747 mole) in 150 ml of diglyme, at −40° to −30° C. After having agitated for one hour, 400 g of a mixture of HFPO/HFP (weight ratio 65:35) are metered in at the rate of 15 l/h at the above specified temperature, agitation is then continued for 24 hours. The reaction mixture is heated to 20° C. Unreacted epoxide and HFP are allowed to escape. This gaseous mixture is practically free from perfluoropropionic acid fluoride - a fact which may stand for a perfect conversion. The work-up is carried out as per example 1, producing by distillation 125 g of perfluoro-α-propoxy-propionic acid fluoride (0.376 mole) having a boiling point of 55° – 57° C

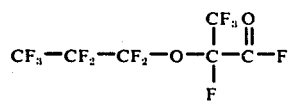

and 96 g of perfluoro-α-[2-(n-propoxy)-propoxy]-propionic acid fluoride (0.197 mole) having a boiling point of 115° – 117° C.

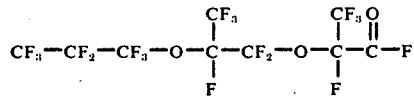

The portion having a higher boiling point amounts to 22 g.

EXAMPLE 6

2 200 g of a mixture of HFPO/HFP (weight ratio 70:30) are introduced by condensation - in analogy to example 1 - into a solution of 500 g of tris-dimethylaminodifluorophosphorane in 500 ml of diglyme at −35° to −30° C and agitated for 47 hours at this temperature. The work-up of the newly formed heavy phase yields 341 g of perfluoro-α-propoxy-propionic acid fluoride having a boiling point of 55° – 57° C (23% of the theoretical yield), 26 g of intermediate fraction having a boiling point of 60° – 115° C and 514 g of perfluoro-α-[2-(n-propoxy) -propoxy]-propionic acid fluoride having a boiling point of 115° – 117° C (34% of the theoretical yield).

The residue having a higher boiling point amounts to 158 g (10% of the theoretical yield). For its larger part it consists of tetramers of HFPO. The yields are calculated on the quantity of epoxide applied.

EXAMPLE 7

1050 g of a mixture of hexafluoropropene epoxide-hexafluoropropene (weight ratio 65:35) are introduced slowly by condensation within 48 hours - as described in example 1 — into a solution of 300 g of tris-dimethylaminodifluorophosphorane in 150 ml of diglyme, at −30° C; the agitation is continued at the same temperature for further 3 days. The work-up is carried out analogously to example 1. There are obtained:

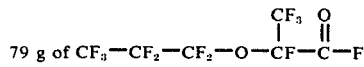

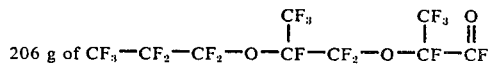

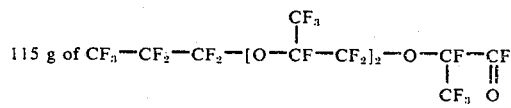

Boiling point: 160° – 164° C.

The portion having a higher boiling point amounts to 29 g.

What is claimed is:

1. A process for preparing perfluoro-α-alkoxypropionic acid fluorides of the general formula $$R^1-O-(CF(CF_3)-CF_2-O)_n-CF(CF_3)-COF \qquad I$$

wherein $R^1$ stands for a perfluoroalkyl radical having from 1 to 9 carbon atoms or for the radical

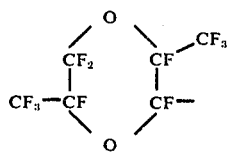

and wherein $n$ is 0, 1 or 2, which comprises that perfluorocarbonyl compounds of the general formula $$R^2-CO-R^3 \qquad II,$$

wherein
$R^2$ represents fluorine or $R_F^2$,
$R^3$ represents fluorine or $R_F^3$ or ($R^2$ being fluorine) also $R_F^3 - OC_F(CF_3)-$,
$R_F^2$ and $R_F^3$ represent identical or different perfluoroalkyl radicals having from 1 to 4 carbon atoms or $R^2$ and $R^3$ combined with the CO group give the compound perfluoro-2-oxo-3,6-dimethyl-1,4-dioxane, are reacted with hexafluoropropene epoxide in the presence of tris-dimethylamine-difluoro-phosphorane in an aprotic polar solvent, at a temperature of −50° to −10° C.

2. The process of claim 1, which comprises that the process is carried out at a temperature of −40° to −20° C.

3. The process of claim 1, which comprises that perfluoro-n-propionic acid fluoride is reacted to yield perfluoro-α- (n-propoxy)-propionic acid fluoride.

4. The process of claim 1, which comprises that perfluoro-α- (n-propoxy)-propionic acid fluoride is reacted to yield perfluor-α-[2-(n-propoxy)-propoxy]-propionic acid fluoride.

5. The process according to claim 4, which comprises that the perfluoro-α-(n-propoxy)-propionic acid fluoride employed is prepared in situ from hexafluoropropene epoxide in the presence of tris-dimethyl-aminodifluorophosphorane in an aprotic polar solvent at a temperature of −50° to −10° C.

6. The process according to claim 1, which comprises that perfluoro-2-oxo-3,6-dimethyl-1,4-dioxane is reacted with hexafluoropropene-epoxide to yield perfluoro-α-(3,6-dimethyl- 1,4-dioxanyl-2-oxy)-propionic acid fluoride.

7. The process according to claim 6, which comprises that perfluoro-2-oxo-3,6-dimethyl-1,4-dioxane is prepared in situ from perfluoropyruvic acid fluoride and hexafluoropropene epoxide in the presence of tris-dimethylamino-difluorosphosphorane in an aprotic polar solvent, at a temperature of −50° to −10° C.

8. The process according to claim 7, which comprises that a molar ratio of hexafluoropropene epoxide/perfluoropyruvic acid fluoride of from 1 to 5 is used.

9. The process according to claim 1, wherein $R^1$ stands for a perfluoro-alkyl radical having from 1 to 9 carbon atoms or for the radical.

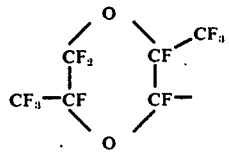

and wherein $R^3$ stands for $R_F{}^3$ or ($R^2$ being fluorine) stands also for $R_{F3} — OC_F(CF_3)—$.

* * * * *